(12) United States Patent
Ben-Ami

(10) Patent No.: US 10,786,268 B2
(45) Date of Patent: Sep. 29, 2020

(54) DEVICE AND METHOD FOR REMOVING OCCLUSIONS IN A BIOLOGICAL VESSEL

(71) Applicant: Triticum Ltd., Ramat-HaSharon (IL)

(72) Inventor: Doron Jacob Ben-Ami, Ramat-HaSharon (IL)

(73) Assignee: Triticum Ltd., Ramat-HaSharon (IL)

( * ) Notice: Subject to any disclaimer, the term of this patent is extended or adjusted under 35 U.S.C. 154(b) by 234 days.

(21) Appl. No.: 15/961,909

(22) Filed: Apr. 25, 2018

(65) Prior Publication Data

US 2018/0235645 A1    Aug. 23, 2018

Related U.S. Application Data

(60) Division of application No. 14/315,352, filed on Jun. 26, 2014, now Pat. No. 9,987,027, which is a continuation-in-part of application No. PCT/IL2013/050049, filed on Jan. 15, 2013.

(60) Provisional application No. 61/586,792, filed on Jan. 15, 2012.

(51) Int. Cl.
*A61B 17/22* (2006.01)

(52) U.S. Cl.
CPC .......... *A61B 17/22031* (2013.01); *A61B 2017/22034* (2013.01); *A61B 2017/22094* (2013.01)

(58) Field of Classification Search
CPC .... A61B 17/22031; A61B 2017/22094; A61B 2017/22034
See application file for complete search history.

(56) References Cited

U.S. PATENT DOCUMENTS

| 4,643,184 A | 2/1987 | Mobin-Uddin |
| 4,765,332 A | 8/1988 | Fischell et al. |
| 5,003,657 A | 4/1991 | Boiteau et al. |
| 5,009,659 A | 4/1991 | Hamlin et al. |
| 5,129,910 A | 7/1992 | Phan et al. |
| 5,133,733 A | 7/1992 | Rasmussen et al. |
| 5,192,290 A | 3/1993 | Hilal |
| 5,370,653 A | 12/1994 | Cragg |
| 5,421,832 A | 6/1995 | Lefebvre |
| 5,522,825 A | 6/1996 | Kropf et al. |
| 5,702,413 A | 12/1997 | Lafontaine |
| 5,769,960 A | 6/1998 | Nirmel |
| 5,827,304 A | 10/1998 | Hart |

(Continued)

FOREIGN PATENT DOCUMENTS

| CA | 2571343 | 2/2006 |
| CN | 1216929 | 5/1999 |

(Continued)

OTHER PUBLICATIONS

Official Action dated Apr. 26, 2019 From the U.S. Patent and Trademark Office Re. U.S. Appl. No. 15/528,110. (19 pages).

(Continued)

*Primary Examiner* — Phong Son H Dang

(57) ABSTRACT

A device for use within an occluded biological vessel and a method of using same to remove occlusion material from a vessel are provided. The device includes an elongated body configured for delivering projections arranged around a distal portion thereof into the biological vessel. Each of the projections includes a leaf-like structure connected to a stem portion having a higher axial rigidity than the leaf-like structure.

8 Claims, 13 Drawing Sheets

(56) References Cited

U.S. PATENT DOCUMENTS

| | | | |
|---|---|---|---|
| 5,836,032 A | | 11/1998 | Hondo |
| 5,895,400 A | | 4/1999 | Abela |
| 5,902,263 A | | 5/1999 | Patterson et al. |
| 5,984,965 A | * | 11/1999 | Knapp ............. A61B 17/22031 604/9 |
| 6,027,514 A | | 2/2000 | Stine et al. |
| D435,944 S | * | 1/2001 | Luoma ......................... D32/14 |
| 6,254,571 B1 | | 7/2001 | Hart |
| 6,350,271 B1 | | 2/2002 | Kurz et al. |
| 6,458,139 B1 | * | 10/2002 | Palmer ................ A61B 17/221 606/113 |
| 6,692,504 B2 | | 2/2004 | Kurz et al. |
| 6,775,873 B2 | | 8/2004 | Luoma |
| 7,008,434 B2 | | 3/2006 | Kurz et al. |
| D532,978 S | * | 12/2006 | Robinson ...................... D4/128 |
| 7,416,555 B2 | * | 8/2008 | Krivoruchko .. A61B 17/320725 606/159 |
| D610,761 S | | 2/2010 | Gengler et al. |
| 7,731,731 B2 | | 6/2010 | Abela |
| 8,021,379 B2 | | 9/2011 | Thompson et al. |
| 8,021,380 B2 | | 9/2011 | Thompson et al. |
| 8,034,095 B2 | | 10/2011 | Randolph et al. |
| 8,062,307 B2 | | 11/2011 | Sepetka et al. |
| D659,918 S | * | 5/2012 | Zach ............................. D32/14 |
| 8,365,337 B2 | * | 2/2013 | Tash ........................ E03C 1/302 15/104.001 |
| 8,545,499 B2 | | 10/2013 | Lozier et al. |
| 8,784,434 B2 | | 7/2014 | Rosenbluth et al. |
| 8,814,892 B2 | | 8/2014 | Galdonik et al. |
| 8,852,205 B2 | | 10/2014 | Brady et al. |
| 9,113,857 B2 | * | 8/2015 | Sethi ................. A61B 10/0283 |
| 9,131,988 B2 | | 9/2015 | Bagwell et al. |
| 9,138,307 B2 | | 9/2015 | Valaie |
| 9,194,114 B2 | | 11/2015 | Petry |
| 9,216,034 B2 | | 12/2015 | Avneri et al. |
| 9,217,243 B2 | | 12/2015 | Gwen |
| 9,220,499 B2 | | 12/2015 | Viola |
| 9,717,519 B2 | | 8/2017 | Rosenbluth et al. |
| 2001/0016962 A1 | | 8/2001 | Moore et al. |
| 2002/0147458 A1 | | 10/2002 | Hiblar et al. |
| 2004/0215222 A1 | | 10/2004 | Krivoruchko |
| 2005/0216050 A1 | | 9/2005 | Sepetka et al. |
| 2006/0184194 A1 | | 8/2006 | Pal et al. |
| 2006/0287667 A1 | | 12/2006 | Abela |
| 2007/0066991 A1 | | 3/2007 | Magnuson |
| 2007/0118165 A1 | | 5/2007 | DeMello et al. |
| 2008/0033423 A1 | | 2/2008 | Peacock, III |
| 2008/0167678 A1 | | 7/2008 | Morsi |
| 2008/0262495 A1 | | 10/2008 | Coati et al. |
| 2009/0054805 A1 | | 2/2009 | Boyle, Jr. |
| 2010/0249815 A1 | | 9/2010 | Jantzen et al. |
| 2011/0144671 A1 | | 6/2011 | Piippo Svendsen et al. |
| 2012/0005849 A1 | | 1/2012 | Tash |
| 2012/0172656 A1 | | 7/2012 | Walters et al. |
| 2014/0135814 A1 | | 5/2014 | Sepetka et al. |
| 2014/0309657 A1 | | 10/2014 | Ben-Ami |
| 2014/0371782 A1 | | 12/2014 | Galdonik et al. |
| 2015/0018859 A1 | * | 1/2015 | Quick ............ A61B 17/320725 606/159 |
| 2015/0119896 A1 | | 4/2015 | Krolik et al. |
| 2015/0164630 A1 | | 6/2015 | Johnson et al. |
| 2016/0051261 A1 | | 2/2016 | Centeno et al. |
| 2016/0221050 A1 | | 8/2016 | Beck et al. |
| 2017/0311966 A1 | | 11/2017 | Ben-Ami |

FOREIGN PATENT DOCUMENTS

| | | |
|---|---|---|
| CN | 1501825 | 6/2004 |
| CN | 101035474 | 9/2007 |
| CN | 102170833 | 8/2011 |
| CN | 104093369 | 10/2014 |
| DE | 102004040868 | 3/2006 |
| GB | 2459481 | 10/2009 |
| JP | 2003-010193 | 1/2003 |
| JP | 2003-038500 | 2/2003 |
| WO | WO 94/023787 | 10/1994 |
| WO | WO 2005/102184 | 11/2005 |
| WO | WO 2012/110619 | 8/2012 |
| WO | WO 2013/105099 | 7/2013 |
| WO | WO 2016/120864 | 8/2016 |

OTHER PUBLICATIONS

Chiu et al. "Permeability of Three-Dimensional Fibrin Constructs Corresponds to Fibrinogen and Thrombin Concentrations", BioResearch Open Access, 1(1): 34-40, Feb. 1, 2012.

Notice of Reason for Rejection dated Aug. 30, 2019 From the Japan Patent Office Re. Application No. 2017-540079 and Its Translation Into English. (8 Pages).

Official Action dated Sep. 26, 2019 From the U.S. Patent and Trademark Office Re. U.S. Appl. No. 15/528,110. (14 pages).

Notification of Office Action and Search Report dated Dec. 20, 2019 From the National Intellectual Property Administration of the People's Republic of China Re. Application No. 201680019053.5 and Its Translation Into English.(19 Pages).

Official Action dated Jan. 16, 2020 From the U.S. Patent and Trademark Office Re. U.S. Appl. No. 15/528,110. (15 pages).

Official Action dated Jul. 17, 2019 From the U.S. Patent and Trademark Office Re. U.S. Appl. No. 15/528,110. (12 pages).

Office Action dated Jun. 6, 2018 From the Israel Patent Office Re. Application No. 233660 and Its Translation Into English. (4 Pages).

Notification of Office Action dated Feb. 3, 2019 From the State Intellectual Property Office of the People's Republic of China Re. Application No. 201610379472.1 and Its Translation of Office Action Into English. (10 Pages).

Advisory Action Before the Filing of an Appeal Brief dated Feb. 26, 2019 From the U.S. Patent and Trademark Office Re. U.S. Appl. No. 15/528,110. (2 pages).

Notification of Office Action dated Aug. 14, 2018 From the State Intellectual Property Office of the People's Republic of China Re. Application No. 201610379472.1 and Its Summary in English. (5 Pages).

Advisory Action Before the Filing of an Appeal Brief dated Aug. 19, 2019 From the U.S. Patent and Trademark Office Re. U.S. Appl. No. 15/528,110. (2 pages).

Notice of Reason for Rejection dated Jan. 7, 2020 From the Japan Patent Office Re. Application No. 2017-540079 and Its Translation Into English. (6 Pages).

Advisory Action Before the Filing of an Appeal Brief dated Sep. 12, 2017 From the U.S. Patent and Trademark Office Re. U.S. Appl. No. 14/315,352. (3 pages).

Advisory Action Before the Filing of an Appeal Brief dated Mar. 20, 2017 From the U.S. Patent and Trademark Office Re. U.S. Appl. No. 14/315,352. (3 pages).

Communication Pursuant to Article 94(3) EPC dated Mar. 10, 2016 From the European Patent Office Re. Application No. 13735641.6.

Communication Pursuant to Article 94(3) EPC dated Jun. 23, 2017 From the European Patent Office Re. Application No. 13735641.6. (5 Pages).

Decision of Rejection dated Dec. 12, 2017 From the Japan Patent Office Re. Application No. 2014-551729. (2 Pages).

Examination Report dated Apr. 12, 2017 From the Instituto Mexicano de la Propiedad Industril, Direccion Divisional de Patentes, IMPI Re. Application No. MX/a/2014/008474 and Its Translation Into English. (6 Pages).

International Preliminary Report on Patentability dated Aug. 10, 2017 From the International Bureau of WIPO Re. Application No. PCT/IL2016/050073. (9 Pages).

International Preliminary Report on Patentability dated Jul. 24, 2014 From the International Bureau of WIPO Re. Application No. PCT/IL2013/050049.

International Search Report and the Written Opinion dated Jul. 19, 2013 From the International Searching Authority Re. Application No. PCT/IL2013/050049.

(56) References Cited

OTHER PUBLICATIONS

International Search Report and the Written Opinion dated Jul. 29, 2016 From the International Searching Authority Re. Application No. PCT/IL2016/050073.
Invitation to Pay Additional Fees dated May 9, 2016 From the International Searching Authority Re. Application No. PCT/IL2016/050073.
Notice of Allowance dated Mar. 2, 2018 From the U.S. Patent and Trademark Office Re. U.S. Appl. No. 14/315,352. (17 pages).
Notice of Reasons for Rejection dated Nov. 15, 2016 From the Japan Patent Office Re. Application No. 2014-551729 and Its Translation Into English. (18 Pages).
Notice of Reasons for Rejection dated May 30, 2017 From the Japan Patent Office Re. Application No. 2014-551729. (5 Pages).
Notification of Office Action and Search Report dated Dec. 4, 2015 From the State Intellectual Property Office of the People's Republic of China Re. Application No. 201380005571.8 and Its Summary of Office Action in English.
Notification of Office Action dated Apr. 1, 2016 From the State Intellectual Property Office of the People's Republic of China Re. Application No. 201380005571.8 and Its Summary in English.
Notification of Office Action dated Jul. 5, 2016 From the State Intellectual Property Office of the People's Republic of China Re. Application No. 201380005571.8.
Notification of Office Action dated Jan. 25, 2018 From the State Intellectual Property Office of the People's Republic of China Re. Application No. 201610379472.1 and Its Translation into English. (12 Pages).
Office Action dated Mar. 7, 2018 From the Israel Patent Office Re. Application No. 233660 and Its Translation Into English. (5 Pages).
Official Action dated Oct. 18, 2017 From the U.S. Patent and Trademark Office Re. U.S. Appl. No. 14/315,352. (13 Pages).
Official Action dated Feb. 22, 2017 From the U.S. Patent and Trademark Office Re. U.S. Appl. No. 14/315,352. (14 pages).
Official Action dated Oct. 25, 2016 From the U.S. Patent and Trademark Office Re. U.S. Appl. No. 14/315,352.
Official Action dated Jul. 28, 2017 From the U.S. Patent and Trademark Office Re. U.S. Appl. No. 14/315,352. (14 pages).
Official Action dated Mar. 31, 2017 From the U.S. Patent and Trademark Office Re. U.S. Appl. No. 14/315,352. (11 pages).
Patent Examination Report dated Sep. 7, 2016 From the Australian Government, IP Australia Re. Application No. 2013208660.
Restriction Official Action dated Aug. 8, 2016 From the U.S. Patent and Trademark Office Re. U.S. Appl. No. 14/315,352.
Supplementary European Search Report and the European Search Opinion dated May 11, 2015 From the European Patent Office Re. Application No. 13735641.6.
Translation of Decision of Rejection dated Dec. 12, 2017 From the Japan Patent Office Re. Application No. 2014-551729. (4 Pages).
Translation of Notice of Reasons for Rejection dated May 30, 2017 From the Japan Patent Office Re. Application No. 2014-551729. (11 Pages).
Translation of Notification of Office Action dated Jul. 5, 2016 From the State Intellectual Property Office of the People's Republic of China Re. Application No. 201380005571.8.
Requisition by the Examiner dated Sep. 28, 2018 From the Innovation, Science and Economic Development Canada, Canadian Intellectual Property Office Re. Application No. 2,860,301. (4 Pages).
Supplementary European Search Report and the European Search Opinion dated Aug. 24, 2018 From the European Patent Office Re. Application No. 16742884.6. (9 Pages).
Notification of Decision of Rejection dated Jul. 22, 2019 From the State Intellectual Property Office of the People's Republic of China Re. Application No. 201610379472.1. (5 Pages).
Notification of Office Action and Search Report dated Jul. 22, 2019 From the State Intellectual Property Office of the People's Republic of China Re. Application No. 201680019053.5 and a Summary of the Notification of Office Action Into English.(19 Pages).
Translation Dated Aug. 11, 2019 of Notification of Decision of Rejection dated Jul. 22, 2019 From the State Intellectual Property Office of the People's Republic of China Re. Application No. 201610379472.1. (5 Pages).
Official Action dated Nov. 1, 2018 From the U.S. Patent and Trademark Office Re. U.S. Appl. No. 15/528,110. (39 pages).
Official Action dated Jan. 23, 2019 From the U.S. Patent and Trademark Office Re. U.S. Appl. No. 15/528,110. (11 pages).
Advisory Action Before the Filing of an Appeal Brief dated Feb. 18, 2020 From the U.S. Patent and Trademark Office Re. U.S. Appl. No. 15/528,110. (2 pages).

\* cited by examiner

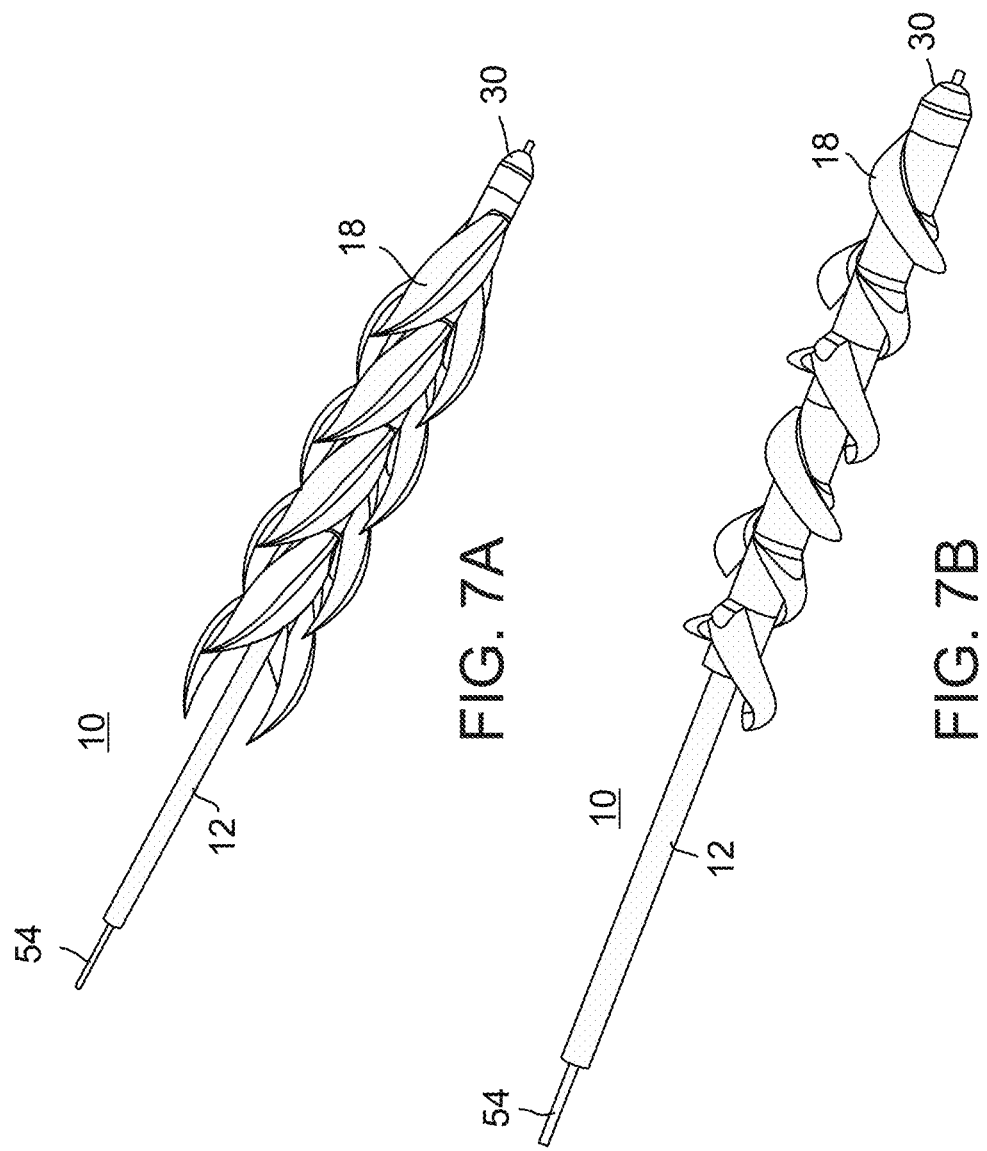

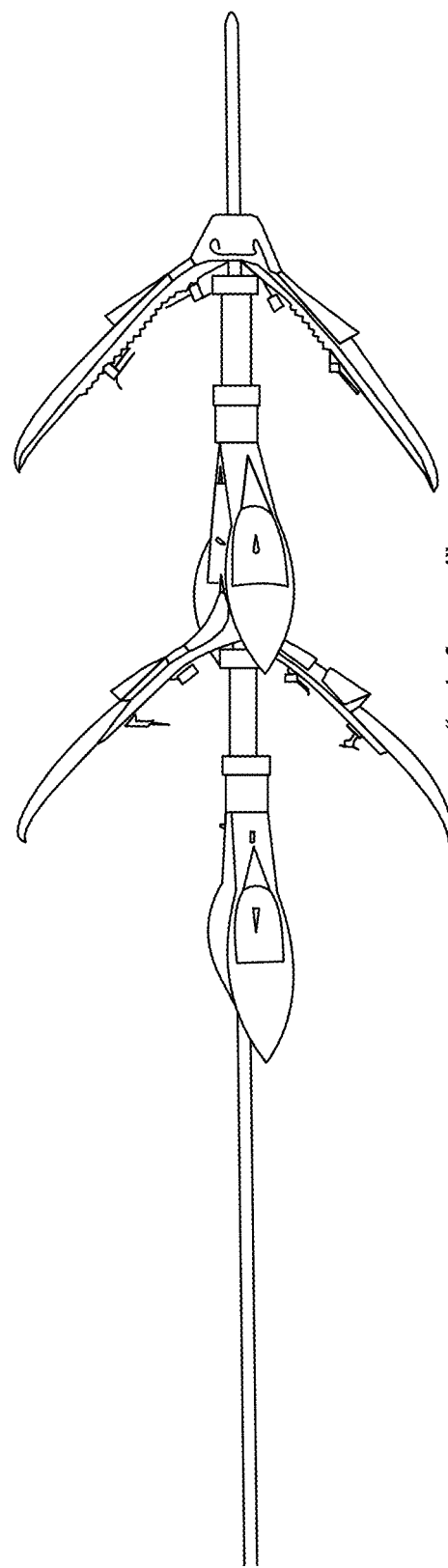
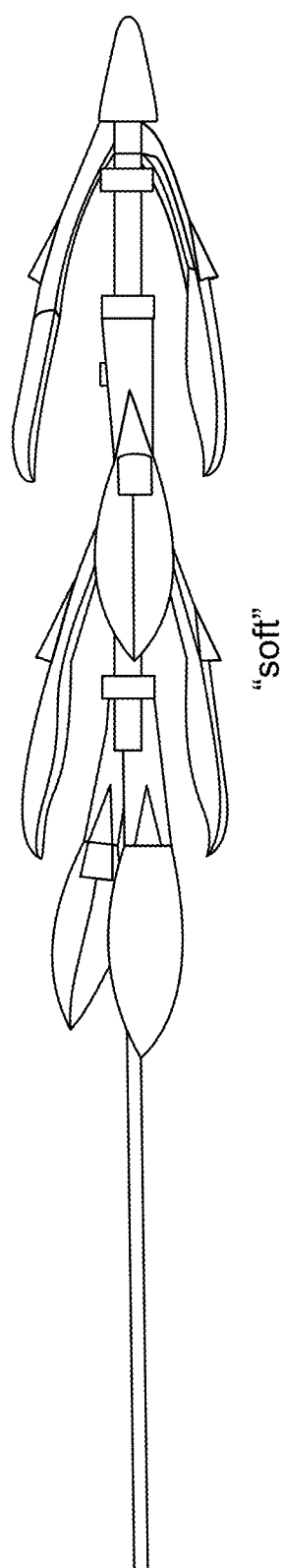
FIG. 8A "reinforced"
FIG. 8B "soft"

DEVICE AND METHOD FOR REMOVING OCCLUSIONS IN A BIOLOGICAL VESSEL

RELATED APPLICATIONS

This application is a division of U.S. patent application Ser. No. 14/315,352 filed on Jun. 26, 2014, which is a Continuation-In-Part (CIP) of PCT Patent Application No. PCT/IL2013/050049, having International Filing Date of Jan. 15, 2013, which claims the benefit of priority under 35 USC 119(e) of U.S. Provisional Patent Application No. 61/586,792 filed on Jan. 15, 2012. The contents of the above applications are incorporated herein by reference in their entirety.

FIELD AND BACKGROUND OF THE INVENTION

The present invention relates to a device for removing occlusions from a biological vessel. Specific embodiments of the present invention relate to a catheter for dislodging and collecting thrombus material from arteries and in particular brain arteries.

The rapid and effective treatment of an ischemic stroke is a key factor in minimizing the morbidity and mortality that may otherwise result from this medical emergency. In Ischemic stroke, thrombotic material causes occlusion of the arterial vessels that supply blood to the brain. In general, the removal of these thrombi from an occluded or partly occluded vessel may be attempted by enzymatically disintegrating the thrombus material via agents such as tissue plasminogen activator (tPA) or alteplase (thrombolysis) by administering, or by mechanically removing the thrombus (thrombectomy).

Two general approaches are utilized for mechanically removing thrombus material from a small blood vessel: a distal approach and a proximal approach.

In the distal approach, the distal end of the retrieval device (typically fitted with a distal basket or snare) is passed through the occlusion and positioned at a distal side thereof. The device is then pulled back (in a proximal direction) while the distal end engages the thrombus material. One example of a commercially-available device employing this approach is the Merci retriever, manufactured by Concentric Medical Inc. and described in U.S. Pat. No. 6,663,650.

In the proximal approach, the distal end of the retrieval device (fitted with a grasper or an aspirator) is brought into contact with the proximal side of the thrombus and the thrombus is then pulled proximally through the vasculature and finally removed from the body. One example of a device utilizing the proximal approach is the Penumbra device, manufactured by Penumbra Inc. and disclosed in EP 1799128.

Although these approaches can be used to at least partially remove thrombus material occluding an artery, such removal can oftentimes be associated with an increased risk of distal emboli and the release of thrombotic debris. In addition, contact of the device with the endovascular wall can cause trauma to the vascular tissues as well as precipitate vasospasm.

As such, it would be highly advantageous to have a thrombus removal device capable of removing thrombus material from biological vessels and in particular brain blood vessels while being devoid of the above limitations.

SUMMARY OF THE INVENTION

According to one aspect of the present invention there is provided a device for use within an occluded biological vessel comprising an elongated body configured for delivering a plurality of projections arranged around a distal portion of the elongated body into the biological vessel, wherein each of the plurality of projections includes a leaf-like structure connected to a stem portion having a higher axial rigidity than the leaf-like structure.

According to further features in preferred embodiments of the invention described below, the projections are angled toward a proximal end of the elongated body.

According to still further features in the described preferred embodiments the projections are capable of folding against the device body when advanced distally through an occlusion in the biological vessel.

According to still further features in the described preferred embodiments the stem portion may include a protrusion for increasing the axial rigidity of the stem portion.

According to still further features in the described preferred embodiments the projections expand radially outward when the device is positioned within an occlusion in the biological vessel and pulled in a proximal direction.

According to still further features in the described preferred embodiments the stem portion of each of the projections may include a protrusion for increasing a drag force on the projections (drag forces will be created mainly by the open projections thereby facilitating radial outward expansion thereof).

According to still further features in the described preferred embodiments the leaf-like portion of the projections may be concave thereby enabling the leaf-lie portion to function as a scoop.

According to still further features in the described preferred embodiments the projections are arranged as single, pairs or more along the distal portion.

According to still further features in the described preferred embodiments the projections are connected to the elongated body via a swivel or a fixed connector or via molding.

According to still further features in the described preferred embodiments the projections is fixed to the elongated body at an angle rotated 0-180 degrees from an adjacent pair of the projections.

According to still further features in the described preferred embodiments the elongated body and the projections are configured for positioning within a blood vessel.

According to still further features in the described preferred embodiments the projections can be pushed and embedded within thrombus material when folded against the elongated body.

According to still further features in the described preferred embodiments the projections are capable of engaging and/or anchoring, dislodging and/or collecting the thrombus material when the projections are embedded within the thrombus and the elongated body is pulled in a proximal direction.

According to still further features in the described preferred embodiments the device is deliverable into the biological vessel through a 1.5-60 F sheath.

According to still further features in the described preferred embodiments the leaf-like structure and the stem portion are co-molded from elastomeric material such as thermoplastic elastomers (TPEs), silicone, other plastics or metal alloys such as Nitinol or combination of materials.

According to still further features in the described preferred embodiments the stem portion includes an element, or structure for increasing the rigidity of the stem portion.

According to still further features in the described preferred embodiments the element is a thickened region or a strut.

According to still further features in the described preferred embodiments the strut is a nitinol strut, thicker embodiment or enhanced structure.

According to still further features in the described preferred embodiments the leaf-like structure and the stem portion are composed of elastomeric material such as thermoplastic elastomers (TPEs), silicone, other plastics or metal alloys such as Nitinol and further wherein the stem portion is composed of a higher rigidity material, different material or combination of materials.

According to still further features in the described preferred embodiments the leaf-like structure of the projections includes an inward curving distal tip.

According to still further features in the described preferred embodiments the inward curving distal tip is capable of hooking into the thrombus material when the elongated body is pulled in a proximal direction.

According to still further features in the described preferred embodiments the inward curving distal tip is configured for minimizing trauma to a wall of the biological vessel when the device is advanced distally or proximally there within.

According to still further features in the described preferred embodiments the device further comprises at least one imaging marker.

According to still further features in the described preferred embodiments the device further comprises two imaging markers at least one of which being attached to the elongated body via an arm extending radially outward from the elongated body.

According to still further features in the described preferred embodiments the device further comprises a lumen extending between a distal end and a proximal portion of said device, said lumen being for enabling blood flow around an occlusion in a blood vessel.

According to another aspect of the present invention there is provided a method of removing a thrombus from a blood vessel comprising: (a) positioning in the blood vessel a device including a plurality of projections, each of the plurality of projections includes a leaf-like structure connected to a stem portion having a higher axial rigidity than the leaf-like structure; and (b) advancing the plurality of projections distally into a thrombus material; and (c) pulling the projections proximally to thereby penetrate, engage, dislodge and collect the thrombus material.

The present invention successfully addresses the shortcomings of the presently known configurations by providing a device for effectively and non-traumatically clearing occlusions in vessels such as blood vessels.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE SEVERAL VIEWS OF THE DRAWING(S)

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIGS. 5A-5D schematically illustrate use of the present device in clearing an occlusion from a vessel.

Figure 6A:
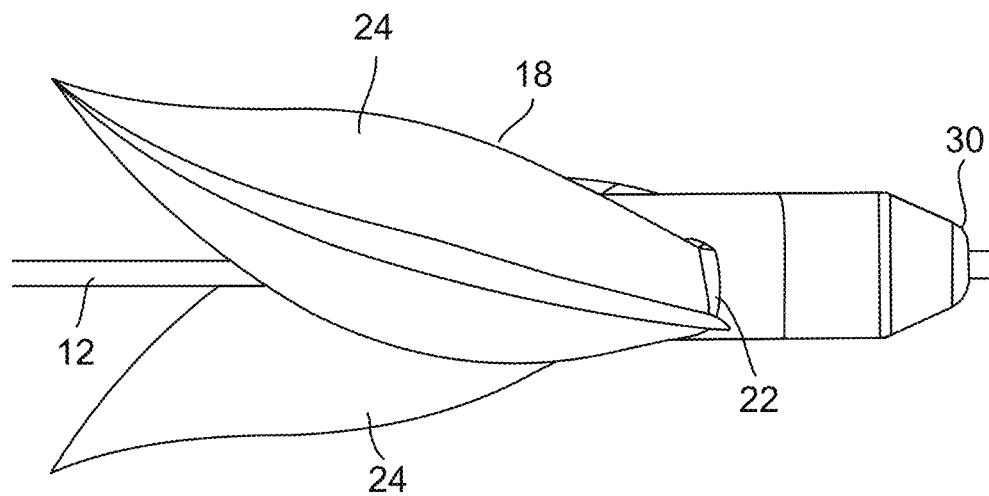
Figure 6B:
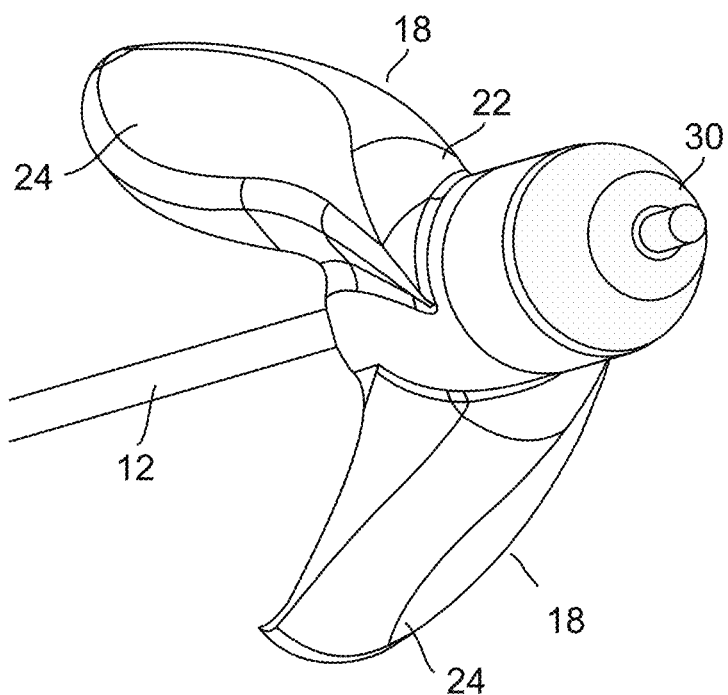
Figure 9:
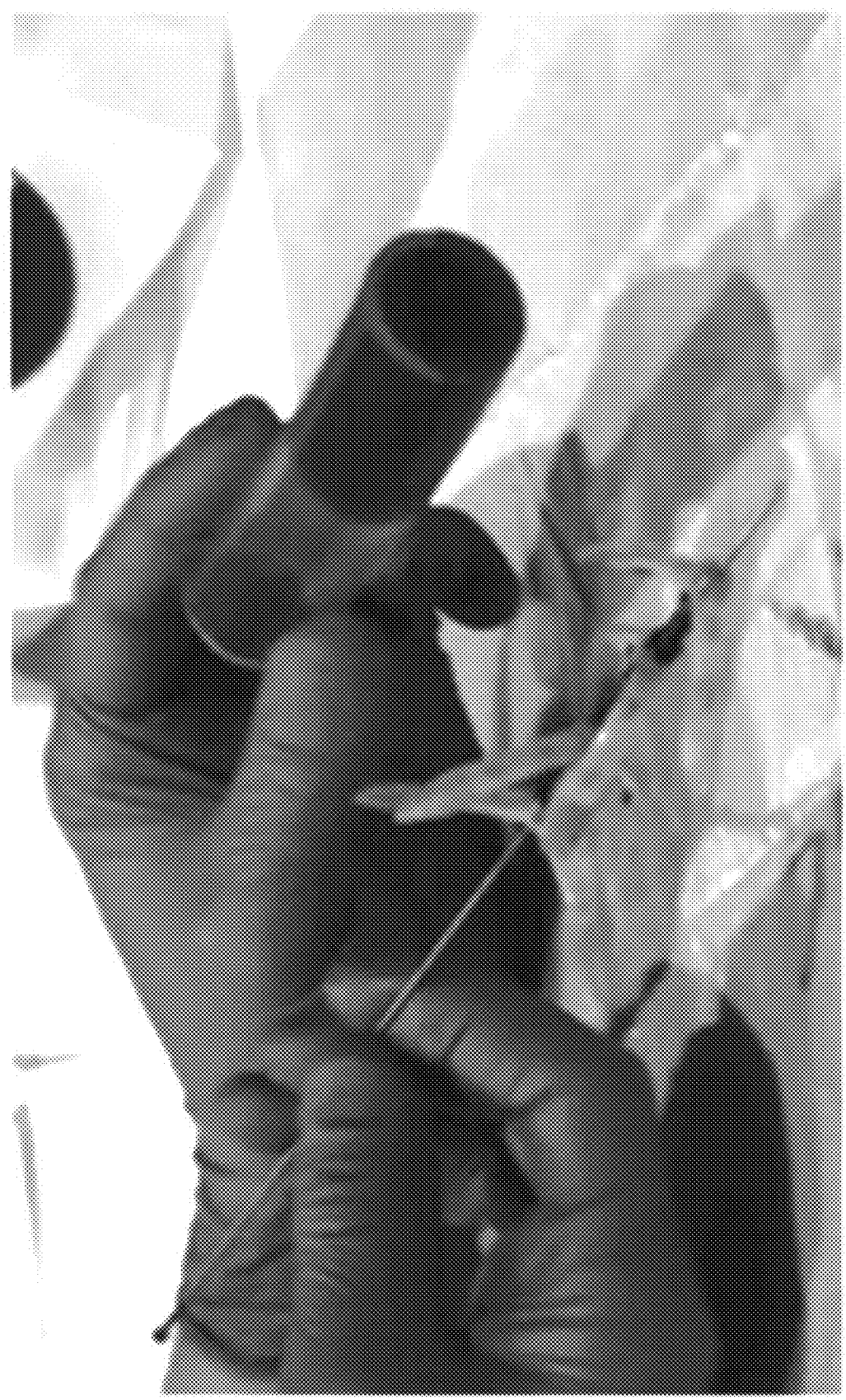

FIGS. 6A-6B illustrate various embodiments of projections which are angled with respect to the device body.

FIG. 7A illustrates an embodiment of the present device having the projections of FIG. 6A.

FIG. 7B illustrates an embodiment of the present device having spirally wound projections.

FIGS. 8A-8B illustrate a prototype of the device of the present invention with reinforced (FIG. 8A) and non-reinforced (FIG. 8B) projections.

FIGS. 9, 10, 11 and 12 illustrate bench testing of the prototypes of FIGS. 8A-8B.

FIGS. 13A-13H illustrate a thrombectomy procedure conducted in a pig using a prototype device constructed in accordance with the teachings of the present invention.

FIGS. 14A-14F are angiograms illustrating results of a pig study conducted with the present device and a prior art thrombectomy device.

Figure 15A:
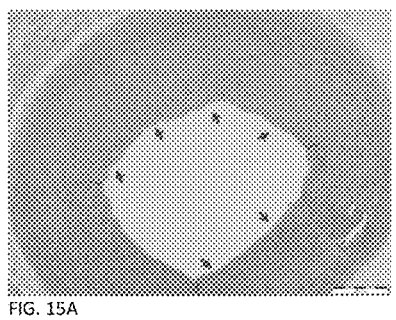
Figure 15B:
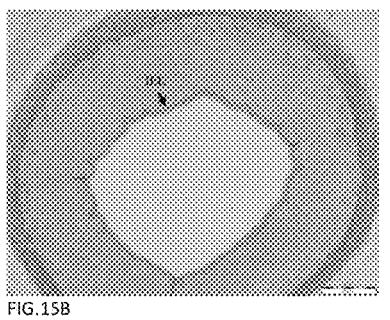
Figure 15C:
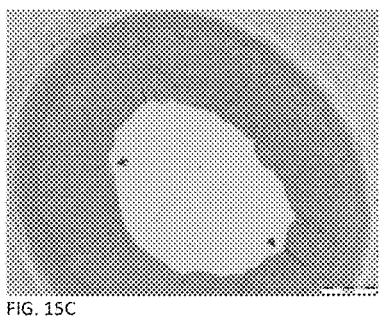
Figure 15D:
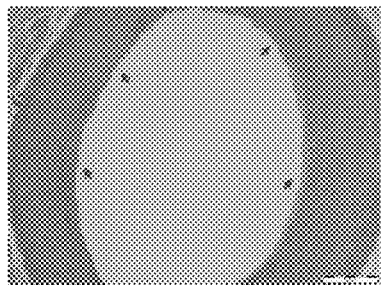
Figure 15E:
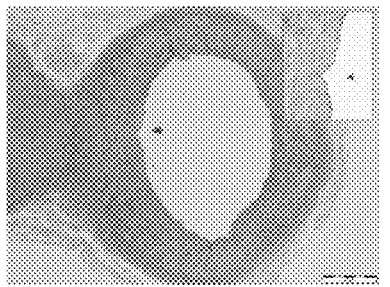
Figure 15F:
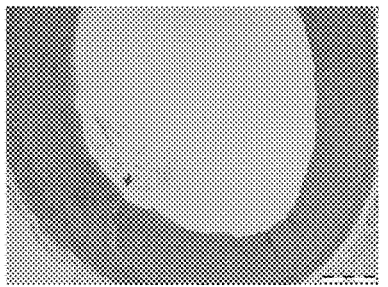

FIGS. 15A-15F are histology slides of arteries catheterized with the present device (FIGS. 15A-15C) and a Nitinol thrombectomy device (FIGS. 15D-15F).

DESCRIPTION OF THE PREFERRED EMBODIMENTS

The present invention is of a device which can be used to clear occlusions from a biological vessel. The present invention is particularly useful for unblocking occluded arteries in the brain.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

In order to effectively clear an occlusion from an artery, thrombus material must be effectively penetrated, engaged/anchored, dislodged and retrieved from the vessel without releasing particles into circulation and while creating minimal irritation/damage to the vessel wall.

In order to maximize thrombus material penetration and dislodgement, catheters having clot retrieval heads which include a plurality of discrete projections have been developed (e.g. U.S. Pat. Nos. 5,895,400, 7,731,731, 5,702,413, 5,827,304, 6,350,271, 6,692,504 or U.S. Pat. No. 7,008,434); however, such catheters may be less effective for retrieving thrombus material or minimizing damage to the vessel wall.

To traverse these limitations of prior art catheters and provide a catheter that is effective at penetrating, engagement, dislodging and retrieving thrombus material, the present inventor devised catheter projections which include a relatively soft leaf-like structure attached to a relatively rigid stem. As is further described herein, the unique structure of the projections of the present catheter maximizes thrombus engagement, dislodgement and retrieval and minimizes trauma to the vessel wall.

Thus, according to one aspect of the present invention there is provided a device for removing occlusions in a biological vessel. As used herein, the phrase "biological vessel" refers to any vessel capable of supporting flow of a biological material. The vessel can be a natural vessel or a synthetic vessel implanted in a body. Examples of vessels include blood vessels such as veins or arteries, lymphatic vessels, urinary system vessels such as the urethra or ureters, seminal vessels, saliva ducts, bile ducts and more.

Occlusions are any flow limiting blockages in the vessel which are caused by local buildup of atherosclerotic material, atherosclerotic emboli, migrating blood clots, biological stones or the like.

The device includes an elongated body for delivering a plurality of projections arranged around a distal portion of the elongated body into the biological vessel. The device can be configured as a catheter for use with a guidewire in clearing thrombus material from a blood vessel. When configured as a catheter, the elongated body can include a longitudinal lumen sized for accepting a guidewire (e.g. 0.014", 0.018" or 0.035" or other guidewires). The lumen can be configured for use with over-the-wire, or rapid exchange systems.

The device can also be delivered within a hollow catheter/delivery tube (guiding catheter). In such cases, the catheter/delivery tube is positioned using a guidewire which is then removed to allow positioning of the present device.

The elongated body can be 10 to 200 cm in length with a width/diameter of 0.5-20 mm when in closed configuration (suitable for delivery within a 1.5-60 F sheath). The elongated body is preferably shaped as shaft (rod or tube) and is fabricated from any bio-compatible material, including, for example, alloys such as stainless steel, Nitinol or polymers such as Polyimide (PI), Polyether Block Amide (PEBA)—Pebax. The elongated body is preferably axially rigid in order to facilitate lodging of the distal portion (carrying the projections) into the occlusion and yet flexible enough to facilitate navigation through torturous vessels while ensuring safety (e.g. blood vessels in the brain). Rigidity of the elongated body (catheter) is same range as catheters commonly used for navigating biological vessels such as blood vessels.

Each projection includes a leaf-like structure connected to a stem portion having a higher axial rigidity than the leaf-like structure. Any number of projections can be carried on the elongated body depending on the biological vessel, occlusion size and type and function of the device. A typical number of projections can range from 1-20 or more.

The stem portions connect the leaf-like structures to the elongated body and are oriented such that leaf-like structures project radially outward and backwards from the elongated body at an angle of 0-90, degrees or above with respect to the longitudinal axis of the elongated body.

The axial rigidity of the stem portion can be preferably anywhere from 0.1-100 grams (e.g. 10-90, 20-80, 30-70, 40-60) or more depending on the occlusion location, occlusion type and size, leaf like structure and material the stem is constructed from. The axial rigidity of the leaf like structures can preferably be anywhere from 0.0-50 grams (e.g. 5-40, 10-30, 20-25) or more depending on the occlusion location, occlusion type and size, leaf like structure and material the leaf is constructed from.

The leaf-like structures and optionally stems are preferably elastically deformable made out of elastomeric material such as thermoplastic elastomers (TPEs), silicone, other plastics or metal alloys such as Nitinol. Elasticity is selected such that when the device is advanced distally into an occlusion (thrombus) within the biological vessel, the projections fold against the elongated body due to the forces exerted by the occlusion/thrombus mass. This enables the projections to penetrate an occlusion (e.g. thrombus) in the vessel without crossing or deploying distally outside to the thrombus mass and lodge therein. When the device is pulled in a proximal direction, the projections deploy outward (to the angle set by the stems or the vessel wall limitation) due to the drag forces exerted by the occlusion (thrombus) mass thereby enabling the device to engage/anchor to the occlusion material, dislodge it from the vessel wall and remove it.

The leaf-like structure can be of any shape and size suitable for collection of occlusion material. The leaf-like structures can be oval-shaped, rectangular/polyangular-shaped, spiral, a combination of several shapes including simple or complex shapes with fractal characteristics.

Typical dimensions for the leaf-like projections can be 0.2-30 millimeter in length, 0.05-20 millimeter in width, 0.03-3 millimeter in thickness, with a single side surface area of 0.01-600 millimeter$^2$.

The stems portions can be 0.1-20 millimeter in length, 0.02-20 millimeter in width, 0.03-3 millimeter in thickness.

The internal surface (facing towards the elongated body) of the leaf-like structure is preferably concave in order to increase the surface area thereof and the drag/resistance force exerted on the internal surface by the thrombus mass. Such a concave configuration also increases the ability of the projections to collect (scoop) the occlusion material. The exterior surface of the leaf-like structure is preferably convex to facilitate delivery within the vessel and lodging of the projections into the occlusion while folded in a "close configuration" (arrow like) due to the drag forces exerted on the leaves-like by the occlusion material when the projections are advanced into the occlusion. Although such a configuration is preferred, internal and external surfaces having alternative contours (e.g. flat on both sides) are also envisaged herein. Each leaf-like structure can also fold in half lengthwise to further improve penetration into the occlusion material.

Folding of the projections and the leaf-like structures occurs during use, in accordance with the mechanical forces exerted upon the projections and the leaf-like portions thereof by the occlusion material and the vessel wall.

The internal surface of the leaf-like structures can also include projections (nanometers to millimeters in height) to increase the surface area and enhance interaction between the leaf-like structures and the occlusion material. Such projections can be simple protrusions or branching, "fractal-like" protrusions which significantly increases the surface area in contact with the thrombus material. The protrusions can project at an angle of 90 degrees or less from the surface and take the form of individual cones, hairs, spines or the like. The protrusions can also be arranged as overlapping scales or as continuous ridges. The protrusions can also form a Gecko-like surface (Mengiic and Sitti "Gecko-Inspired polymer Adhesives", Polymer Adhesion, Friction, and Lubrication, First Edition).

The internal surface of the leaf-like structures can also include depressions (e.g. pores, channels). In any case, the protrusions or depressions can be an order of magnitude smaller than the size of the leaf-like structure (e.g. protrusions in a leaf-like structure 10 mm long can be 1 mm in length).

The protrusions/depressions can be arranged in a fractal-like order with a parent protrusion/depression surrounded by scaled-down protrusions/depressions. For example, a 10 mm long leaf-like structure can include 1 mm long primary protrusion surrounded by several "sub-protrusion" that are 0.1 mm in length (and so forth).

Such structuring of the internal surface of the leaf-like structures can improve complete retrieval of the thrombus in its in-situ form and thus can minimize the risk of embolism as a result of particles "escaping" from the thrombotic mass.

The distal portion (tip) of the leaf-like structure is preferably curved inward in order to minimize trauma/damage to the vessel when the device is navigated within the blood vessels. To further decrease trauma and irritation to the vessel wall, the tips can be fabricated from a very soft material (softer than the rest of the leaf-like structure).

The inward curving tips can also facilitate hooking of the projections into the occlusion material.

The unique configuration of projections of the present device provides several advantages in clearing occlusions in a biological vessel.

(i) Delivery and penetration of occlusion material—when the present device is advanced in a distal direction the contour of the external surface and elasticity of the leaf-like structures enable folding of the projections which reduces the profile of the device and also streamlines the outer surface of the folded projections. This enhances delivery and minimizes disruption of the occlusion (which can lead to release of embolic particles).

(ii) Engagement/anchoring of occlusion material—when the present device is pulled in a proximal direction, drag forces are applied to the inner surfaces of the leaf-like structures and cause the projections to open. This increases the cross sectional area of the device and its surface interaction with the occlusion. In addition, exposure of the inward curving tips to the occlusion material, increases penetration and lodging of the projections in the occlusion material. The stem portion prevents the projections from flipping over thereby ensuring that a pulling force at the handle/proximal part of the device is efficiently converted to engagement/anchoring force.

(iii) Dislodgement of occlusion material—the pulling force at the handle/proximal part of the catheter is also efficiently converted to a proximal movement of the catheter-occlusion complex. The projections can be designed such that the forces applied thereby are matched to the type and location of occlusion. The forces applied by the projections on the occlusion are a function of the occlusion material, size and the properties of the occlusion and the vessel surrounding it, thus minimizing unnecessary force and distortion of the thrombus natural configuration.

(iv) Removal of occlusion—the increased surface area, and the multiple contact areas (at plurality of projections), as well as the unique scoop-like shape of the internal surface of the leaf-like structures facilitate collection of dislodged material. The occlusion material is trapped by the device (projections) creating a catheter-thrombus complex that can be removed as one piece.

The present invention is described in greater detail hereinbelow with reference to the embodiment shown in FIGS. 1-4.

Referring now to the drawings, FIGS. 1-4 illustrate one embodiment of the present invention which is referred to herein as device 10.

Device 10 is configured suitable for entering, engaging/anchoring, dislodging and collecting thrombus material from a blood vessel and in particular small blood vessels of the brain.

Device 10 includes an elongated body 12 having a handle 14 (user engaged portion) at proximal end 16 and projections 18 (12 shown) attached to a distal portion 20. Elongated body 12 includes a nose cone 30 for facilitating non-traumatic delivery into a vessel and also allows penetration into the occlusion/thrombus.

Figure 4:
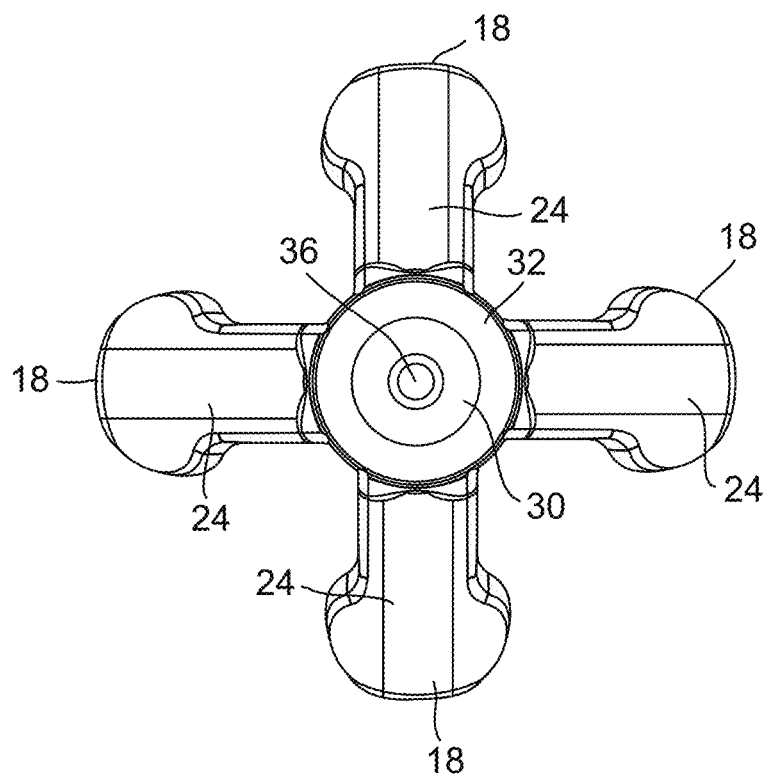
FIG. 4 is a frontal view of one embodiment of the present device showing rotation offset between two pair of projections.

Projections 18 are preferably arranged as single or pairs (arrangements including 3, 4, 5, 6 or more projections are also possible) around distal portion 20, with each single or pair rotated 0-180 degrees from an adjacent single pair. FIG. 4 is a frontal view of device 10 showing two pairs of projections 18 arranged with a 90 degree rotational offset between pairs.

Figure 1:
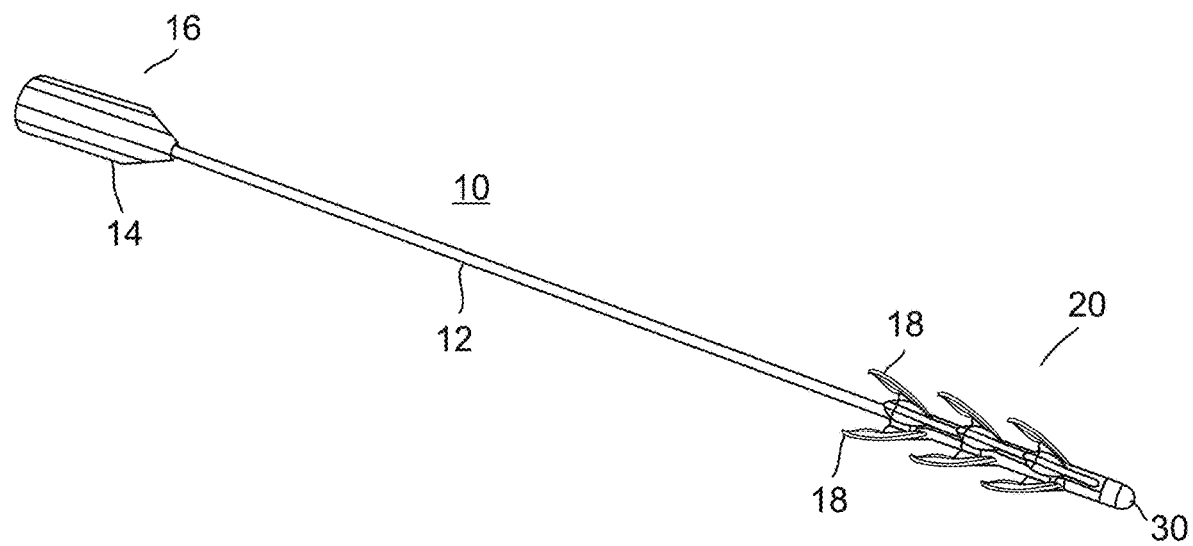
FIG. 1 illustrates one embodiment of the present device.
Figure 2:
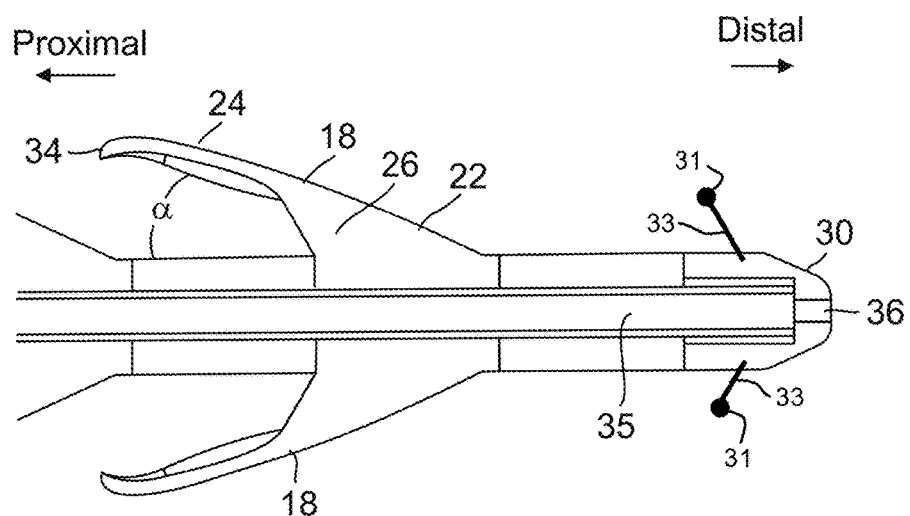
FIGS. 2-3 illustrate a pair of projections in a side view (FIG. 2) and an isometric view (FIG. 3).
Figure 3:
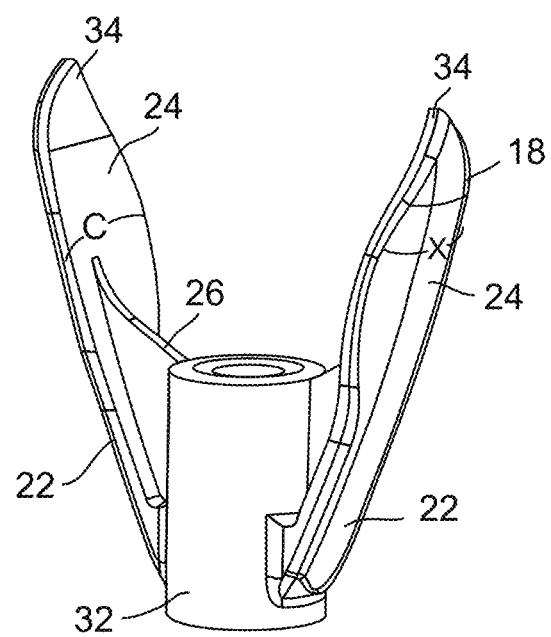

FIGS. 2-3 illustrate one pair of projections 18 in greater detail. Each projection 18 includes a stem portion 22 which is attached to a leaf-like structure 24. As is mentioned hereinabove, the axial rigidity of stem portion 22 is greater than that of leaf-like structure 24. Such increased axial rigidity can be achieved by fabricating stem portion 22 from a more rigid material, by making stem portion 22 thicker than leaf-structure 24 or by providing stem portion 22 with a rigidifying strut (e.g. Nitinol/stainless steel strut co-molded with stem portion 22). In the embodiment shown in FIGS. 1-4, stem portion 22 includes a thickened portion 26 which serves to both increase rigidity thereof and limit the angle of stem portion 22 with respect to the longitudinal axis of elongated body 12, such that outward deployment of projections 18 is limited to a preset angle α (FIG. 2) set by portion 26. Portion 26 is also rigid enough to prevent projections 18 from flipping over (angling towards the distal direction). As is shown in FIGS. 2-3, leaf-like structure 24 includes an inward curving tip 34 for minimizing damage or irritation to the vessel wall when device 10 is pushed and pulled within the vessel. Inward curving tip 34 also functions to facilitate lodging of projections 18 into occlusion material (e.g. thrombus material) when device 10 is pulled in a proximal direction.

As is shown in greater detail in FIG. 3, leaf-like structures 24 are preferably concave (C) at an internal surface thereof and convex (X) on the opposite surface. When in proximal movement after engaged to the thrombus mass the concave shape of the inner surface allows a higher surface contact area and higher drag forces. In addition, leaf-like structure 24 scoops the occlusion material dislodged from the vessel wall.

When moving distally and penetrating the thrombus mass the convex shape produces less drag forces. The concave shape also allows projections 18 to fold into a compact streamlined configuration for delivery into the vessel and occlusion. Additional hydrodynamic streamlining of projections 18 may be effected by providing the outer surface thereof with one or more bumps/protrusions/channels etc. Projections 18 can be individually attached to elongated body 12 via gluing or mechanical couplers. Preferably, projections 18 are attached to elongated body 12 via a fixed or swivel coupler or via molding. For example, two stem portion 22 can be co-molded with a cylindrical coupler 32 (FIG. 3) which can be fitted around elongated body 12 and fixedly attached thereto or allowed to swivel. Leaf-like projections can then be glued or mechanically coupled to the distal end of stem portions 22—or just molded as one piece from the same material.

Projections 18 can be fabricated from a single material or from two or more materials. For example, in the embodiment shown in FIGS. 1-4, projections can be molded from a single material (e.g. silicone, teflon, nylon and any other elastomer, metal alloys such as Nitinol or elastomer with combination with metal alloys such as Nitinol), with the differential rigidity provided by varying the durometer of the material (e.g. molding stem portion 22 from a different structure, a silicone having a higher Shore A value or increased thickness, or by using a different material or a combination of different materials).

Device 10 can further include a web like element interposed between projections 18. Such an element can supplement the ability of device 10 to capture/harvest dislodged occlusion material.

As is mentioned hereinabove, the embodiment of device 10 of FIGS. 1-4 is configured for use in clearing obstructions in a blood vessel, preferably a small brain artery that is 0.5-7 millimeter in diameter. As such, elongated body 12 of device 10 is preferably 10-200 centimeter in length, 0.5-7 millimeter in diameter when in closed configuration, while projections 18 are preferably 0.2-30 mm in length. The length of leaf-like structures is preferably 0.1-30 mm and the width (at the widest thereof) is preferably 0.05-20 mm. Stem portion 22 is preferably 0.1-20 mm in length and 0.02-20 mm in width (at the base).

Projections 18 can be folded against elongated body 12 to an overall diameter of 0.5-7 millimeter. When folded, device 10 can be packed into a 1.5-60 F sheath for delivery through an access site. Once pushed out of the sheath, projections 18 are folded outward to a position constrained by stem portion 22 (or vessel wall) while distal portion 20 is advanced to the site of occlusion. Since leaf-like structure 24 includes a non-traumatic tip 34, advancing device 10 in the distal direction (towards occlusion) does not traumatize or irritate the vessel wall. Once in position, pulling on handle/proximal catheter part 14 deploys projections 18 to angle α as limited by stem portions 22 or the vessel wall. In the deployed position, leaf structures 24 are displaced up to 90 degrees (or more) from the longitudinal axis of elongated body 12 (as limited by stem portion 22) to nearly contact or contact the wall with tip 34 angling inward to eliminate trauma and irritation to vessel wall.

The flexible nature of the leaves-like permits the device to automatically adapt to the caliber of the blood vessel in which device 10 is situated.

Stem portion 22 and/or leaf-like structure 24 can also be configured such that when folded against elongated body 12, the longitudinal axis of leaf like structure 24 is angled with respect to the longitudinal axis of elongated body 12 (FIGS. 6A-6B). This increases the exposure of the internal surface to the biological fluid in the vessel and to the occlusion material and increases drag and likelihood of deployment when device 10 is pulled in a proximal direction.

FIGS. 6A-6B illustrate alternative angulations of projections 18. As is shown in FIG. 6A, projections 18 can be angled laterally (angle range 0-90 degrees) relative to the device main long axis (yaw). This will prevent full symmetry and overlapping of the leaves when in closed configuration and in backward (proximal) movement. The lack of symmetry exposes the inner surface area of leaf-like structures 24 to the occlusion to initiate opening of projections 18. A device 10 having such projections 18 is shown in FIG. 7A.

A roll angle can also be added such that each leaf-like structure 24 has an "angle of attack" (FIG. 6B) relative to the movement vector (angle range 0-90 degrees) i.e. to the anterior edge of leaf-like structures 24 relative to movement of device 10. The angle of attack in the forward motion (when device 10 is pushed towards occlusion) will have hydrodynamic features and a curve design that will ensure an ability to optimally penetrate and minimally disrupt the thrombus structure.

When the device is pulled proximally, the angle of attack (which is the opposite edge) can be shaped in a more acute curve structure in order to allow optimal drag forces of the thrombus on each leaf-like structure 24 thereby ensuring opening of projections 18. Projections 18 can also be configured to spiral around elongated body 12 as is shown in the example of FIG. 7B.

The size shape and properties of projections 18 can be configured according to the blood vessel and occlusion properties. There are two type of thrombus occlusions, a 'red' thrombus (fresh, acute whole blood thrombus) and a 'white' thrombus (relatively chronic embedded with cholesterol and calcium). Projections 18 of device 10 have rigidity properties at a range matching the viscosity ranges of the thrombus.

When configured as a catheter, device 10 includes a lumen 35 which terminates at opening 36. Lumen 35 is configured for accepting a guidewire for guiding device 10 to a target occlusion within a vessel. Lumen 35 can traverse the entire length of elongated body 12 (when use with an over-the-wire system) to an guidewire inlet opening in a proximal end of elongated body or alternatively, lumen 35 can traverse a portion thereof (when used with a rapid exchange system) to a guidewire inlet opening at a side wall along a length of elongated body 12.

Lumen 35 can also include one or more holes or other opening along a portion of elongated body proximal to projections 18. Such holes can be in fluid communication with an opening at tip 30 and would thus enable blood to flow around the occlusion mass once projections 18 penetrate the occlusion and tip 30 crosses the occlusion and is positioned at its distal side.

This will allow reperfusion of the ischemic brain tissue located distally to the occlusion site. The relatively low flow of blood (through the catheter) provides controlled low flow, low pressure reperfusion to the Penumbra brain tissue which is at a metabolic "shutdown" state and thus might be vulnerable to high pressure systolic blood flow. This will prepare the tissue for restoration of full flow following removal of the thrombus.

In cases where delivery is effected through a catheter or guide tube (guiding catheter), delivery and navigation of device 10 can be effected without a guidewire.

In any case, handle 14 (or proximal portion of elongated body 12) is used to guide device 10 (whether over a wire or not) through the vessel and position distal portion 20 at a site of occlusion.

Use of device 10 in clearing a thrombus in a blood vessel is described in greater detail below with reference to FIGS. 5A-5D.

Device 10 can also include radio-opaque markers (e.g. gold, platinum, iridium or combined with the polymer itself or other radio-opaque markers) mounted on the distal end of elongated body 12 (near tip 30).

Markers 31 can be mounted on ends of foldable arms 33 (e.g. Nitinol, platinum, other metal alloy or polymer wires) extending radially outward from elongated body 12. (FIG. 2) When distal portion 20 is positioned outside of the occlusion, markers arms 33 extend out and thus when visualized (fluoroscopy) markers 31 are a predetermined distance apart (e.g. several millimeters). When distal portion 20 is positioned inside an occlusion, markers arms 33 fold against elongated body 12 and thus when visualized (fluoroscopy) the distance between markers 31 is reduced.

Alternatively, one of the markers can be mounted on a foldable arm extending radially outward from elongated body 12, while the second marker can be attached to elongated body 12. When distal portion 20 is positioned inside an occlusion, the marker arm is folded against elongated body 12 and brought into proximity to the second marker. The distance between the markers can be visualized (fluoroscopy) to determine the extent of folding of the arm.

Still alternatively, one or more markers can be fixed to one or more tips 30, such that when distal portion 20 is positioned within an occlusion, folding of projection(s) 18 carrying the marker can be used to determine a distance between tip 30 and elongated body 12 or between a pair of tips 30.

Marker material (e.g. iridium or platinum) can also be included in the material used to fabricate projections 18 or leaf-like structures 24 in order to facilitate identification thereof by a surgeon.

In any case, the markers assist the clinician in determining the correct placement of device 10 within a blood vessel and indicate when distal portion 20 enters an occlusion and projections 18 are lodged therein.

In order to increase the ability of leaf-like structures 24 to collect occlusion material, the internal surface thereof can be coated with a substance that can bind the occlusion material. For example, in the case of a thrombus occlusion, the internal surface of leaf-like structure 24 can be coated with fibrin.

Figure 5A:
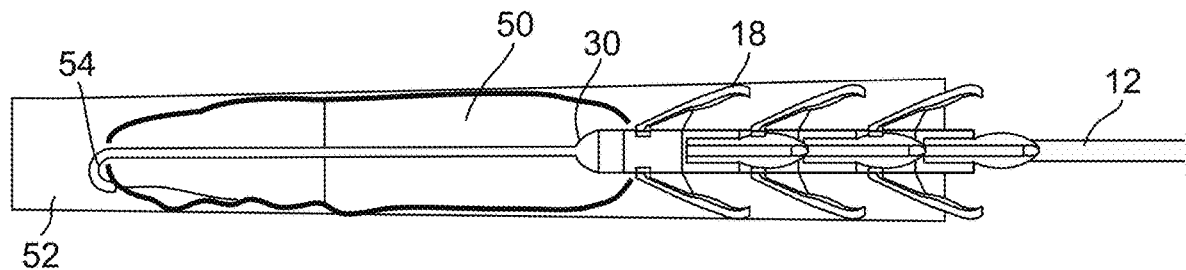
Figure 5B:
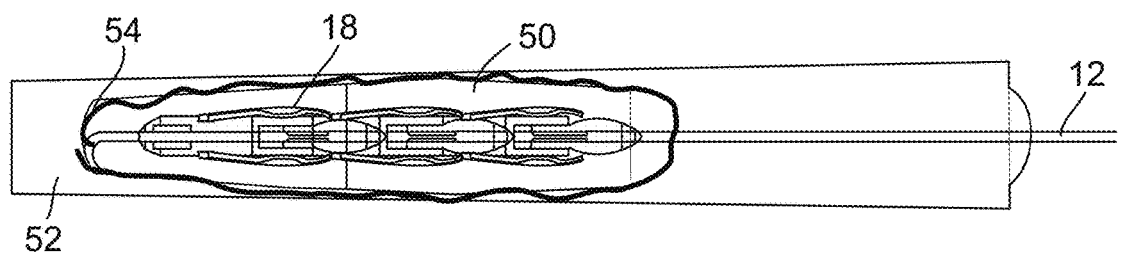
Figure 5C:
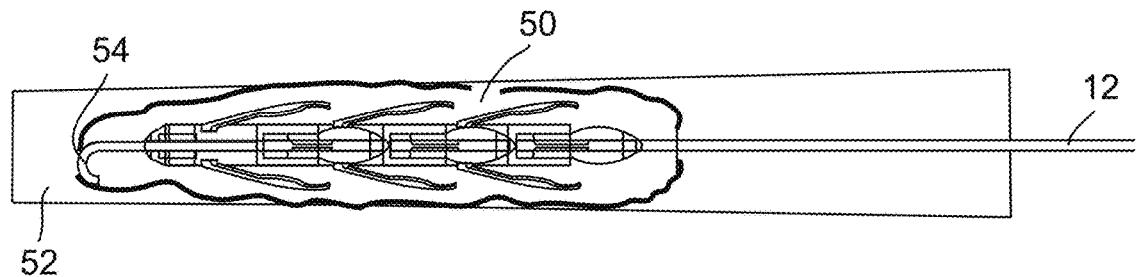
Figure 5D:
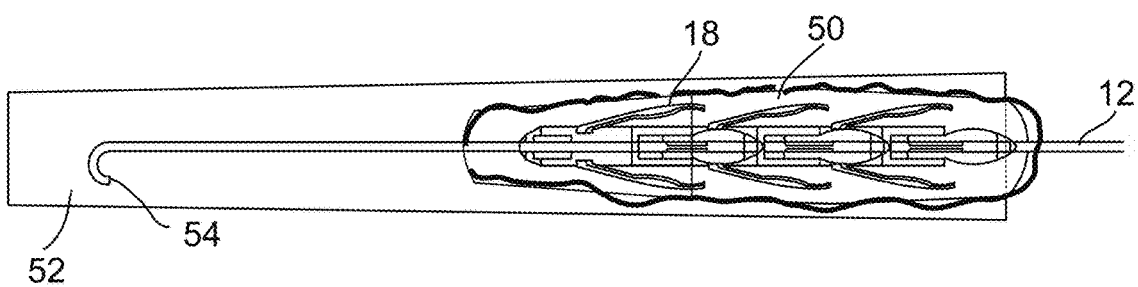

Device 10 of the present invention can be used to clear any type of occlusion in any vessel. FIGS. 5A-5D illustrate use of device 10 in clearing a thrombus in an artery. A guide catheter or guidewire is advanced from an access site (e.g. in a femoral artery) to the carotid artery under angiography. Device 10 is then inserted over-the-wire or through the guide catheter and navigated to the site of the thrombus (FIG. 5A). The surgeon then advances the distal end of device 10 into the thrombus (FIG. 5B) until the distal end of device 10 reaches the distal end of the thrombus (as visualized via the radio-opaque markers described above). The surgeon then applies a gentle pulling force on device 10 to open projections 18 and lodge and engage/anchor them within the thrombus. The device is then pulled along with the trapped thrombus (FIG. 5C).

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following example, which together with the above descriptions, illustrate the invention in a non limiting fashion.

Example 1

Bench Testing of a Prototype

Several prototypes of the device of the present invention were constructed by mounting 4 pairs of 30 mm long and 8 mm wide silicone projections (10 mm stem portion and 20 mm leaf like structure) on a stainless-still rod 1 millimeter in diameter. Two types of projections were tested, 'soft' projections fabricated from 70 Shore silicone (FIG. 8B) and reinforced projections fabricated from 70 Shore silicone and including a 20 mm plastic strut fixed to the stem portion and a portion of the leaf-like structure of each projection (FIG. 8A). Two configurations of projections were tested, pairs arranged with a 90 degree rotational offsets, and pairs arranged with a 45 degree rotational offset.

The total diameter of the device was 25 mm when the projections were in the open configuration (FIG. 8A) and 10 mm when in the closed configuration (FIG. 8B).

The device prototypes were tested for the ability to remove a blood clot from a tube.

Fresh human venous blood was drawn from cubital fossa vein and was mixed for 10 seconds with human thrombin (BioPharm Laboratories, LLC, Bluffdale, Utah, USA) at a ratio of 25 IU to 10 ML whole blood and was incubated for 60 minutes at room temperature inside cylindrical transparent tubes having the following dimensions:

(i) Length: 100 millimeter; internal diameter: 25 millimeter (ii) Length: 100 millimeter; internal diameter: 20 millimeter The resulting blood clot had the following dimensions:

(i) Length: 40 millimeter; diameter of 25 millimeter (ii) Length: 60 millimeter; diameter of 20 millimeter In total, 6 clot occlusions were prepared (3 in each of the tubes described above).

Figure 10:

Each device prototype (FIG. 9) was advanced into the tube to penetrate the proximal clot mass until the distal tip of the device reached the distal (end) of the clot mass (FIG. 10).

Figure 11:

In total, 6 clot penetrations were conducted:

(i) four with the "enforced" catheter prototype: 3×25 millimeter thrombus diameter and 1×20 millimeter thrombus diameter; and (ii) two with the "soft" catheter prototype: 2×20 millimeter thrombus diameter It was observed that while penetrating the clot mass, the projections folded into a closely packed configuration (FIG. 11).

Figure 12:

The device prototypes were then pulled in the proximal direction dislodging the clot mass and collecting it out of the tube (FIG. 12).

It was observed that movement of the device in the proximal direction opened the projections outward from the central rod thereby facilitating scooping of the clot material.

In all 6 tests (two types of tubes, two device prototypes) the device prototypes collected the entire clot mass in one pass.

Example 2

Animal Study 1

An 80 Kg female swine was anesthetized and a mid-line laparotomy was conducted to expose the retro peritoneal space and allow aortic puncture. A 16 F introducing sheath was delivered into abdominal infra-renal aorta using the Seldinger approach.

Figure 13A:
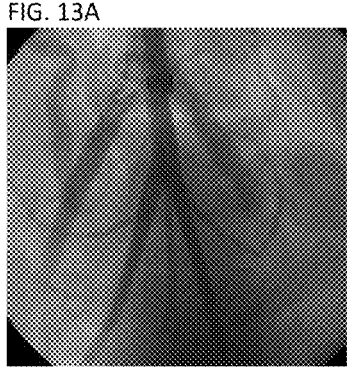

A thrombus measuring approximately 2 cm in length and 5 mm in diameter was prepared from autologous whole blood incubated with Barium (10 cc whole blood to 1 g of Barium sulfate) for two hours at room temperature using a method previously described by Kan L, et al. A novel method of thrombus preparation for use in a swine model for evaluation of thrombectomy devices. AJNR Am J Neuroradiol. 2010 October; 31(9):1741-3). The thrombus was introduced into the sheath and delivered into the left internal iliac artery under fluoroscopy (FIG. 13A).

Figure 13B:
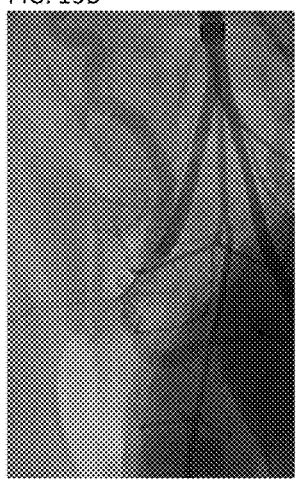
Figure 13C:
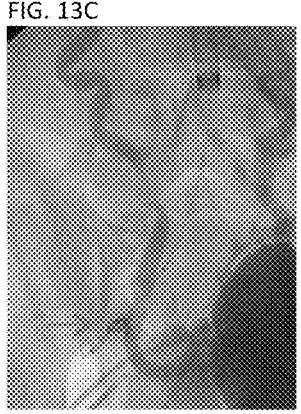
Figure 13D:
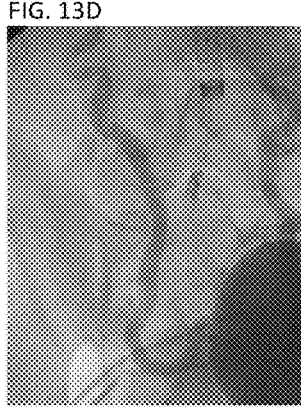
Figure 13E:

An occlusion of the left internal iliac artery was demonstrated via angiography (FIG. 13B).

A prototype catheter was fabricated using a 70 Shore silicone mixed with 10% radio opaque Barium sulfate. The prototype length was 42 mm with a diameter in its neutral configuration measured 5 mm. The prototype included 8 pairs of 5 mm long leaf-like projections.

Figure 13F:
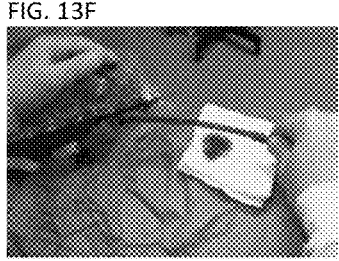
Figure 13G:
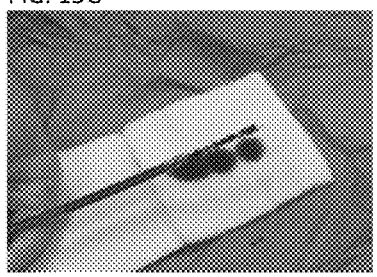

The catheter was navigated over a guidewire and into the occluded vessel and thrombus under fluoroscopic guidance. Approximately one minute following engagement between the catheter head and the thrombus, the catheter was gently pulled back (proximately) under fluoroscopy and retrieval of the thrombus material was observed. The catheter with engaged thrombus material were pulled into the introducing sheath (FIGS. 13C-13E) and then removed from the artery (FIG. 13F). The thrombus material was visualized engaged to the catheter head outside the body (FIG. 13G).

Figure 13H:
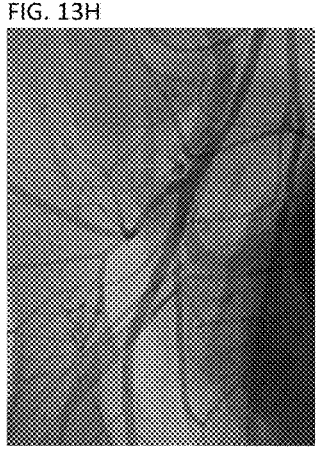
Figure 14A:
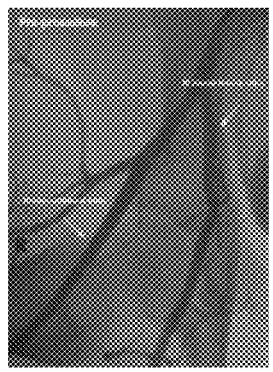
Figure 14B:
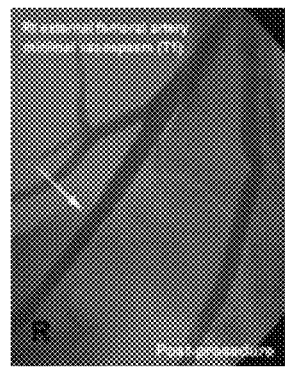
Figure 14C:
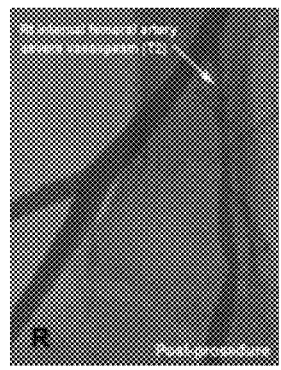
Figure 14D:
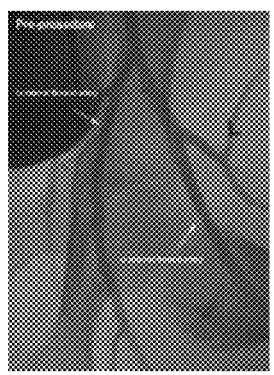
Figure 14E:
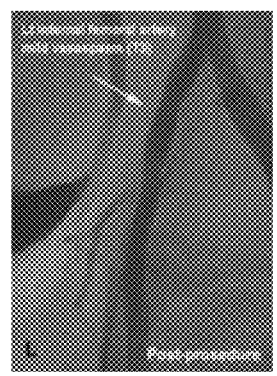
Figure 14F:
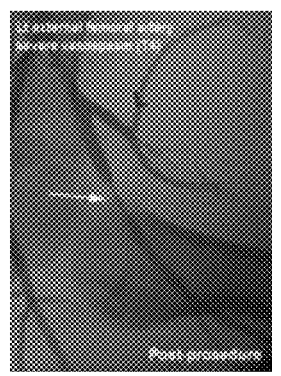

A control angiography demonstrated that the occlusion was removed and that blood flow was restored to the left internal iliac artery with no filling defects. A moderate yet smooth narrowing of the vessel was demonstrated as a result of a moderate vasospasm which resolved later (FIG. 13H).

Example 3

Animal Study 2

A pig study was conducted in order to demonstrate the safety feature of the present device during artery passage and to compare device safety with Nitinol spiral-shaped stent retriever commonly used in thrombectomy procedures.

Materials and Methods

An 81 Kg female swine was anesthetized and a mid-line laparotomy was conducted and the retro peritoneal space was exposed to allow aortic puncture. The Seldinger's technique was used to deliver a 16 F introducing sheath into the abdominal infra-renal aorta to enable subsequent arterial access and catheterizations of the target vessels. The anatomy of the distal aorta, iliac and femoral arteries was demonstrated via angiography (FIGS. 14A and 14C) and the internal diameter (ID) of the target arteries was measured using standard calibrated techniques. The following arteries were used for the procedures:

(i) Right External Femoral artery (distal) (T1); average ID 4.2 mm—present device (ii) Right Internal (Deep) Femoral artery (T2); average ID 4.0 mm—nitinol based device (iii) Left Internal (Deep) Femoral artery (T3); average ID 4.2 mm—present device (iv) Left External Femoral artery (distal) (T4); average ID 4.2 mm—nitinol based device The present device was fabricated from a 70 Shore silicone and was 5 mm in diameter with projections in the open (neutral) configuration; the recommended target vessel ID: 4.0-5.0 mm. The Nitinol based device: was 6 mm diameter in the open configuration; recommended target vessel ID: 3.0-5.5 mm.

The present device was guided over the wire through a 16 F introducer and into the target vessels (T1 and T3) under fluoroscopy using standard catheterization technique. Three consecutive forward and backward passes were made in the target vessels.

The Nitinol based device was guided through a 16 F introducer and into the target vessels (T2 and T4) under fluoroscopy using standard catheterization technique. Three consecutive backward passes were made in the target vessels while the device was in an open configuration. Forward repositioning of the device was made following re-sheathing of the device into a micro-catheter.

The target vessels were surgically removed, flushed and fixed in formaldehyde, and marked with proximal and distal markers.

The excised vessels were sent to a pathology laboratory for Histological analysis primarily of the endothelial layer and the internal elastic lamina of all samples.

Results

Angiography

A control angiography was performed following catheterization of each target vessel. Minimal to mild vasospasm was observed in arteries T1, T3 (present device, FIGS. 14B and 14E) and a severe vasospasm was observed in arteries T2, T4 (Nitinol device, FIGS. 14C and 14F).

Histological Findings

The excised blood vessels appeared to be within normal ranges. Occasional foci of hemorrhage were present in the adventitia. A semi-quantitative histological assessment was employed. Samples were evaluated for endothelial erosion, fibrin deposition, thrombus formation, continuity of the internal elastic lamina (IEL), medial lesions (tearing, necrosis, and inflammation) and lesions in adventitia. The specific parameters were scored as shown in Table 1 below (unless otherwise indicated): 0=Absent, 1=Minimal, 2=Mild, 3=Moderate or 4=Severe.

TABLE 1

Semi-quantitative scoring of artery lesion parameters

| | Scored Parameter | | | | |
|---|---|---|---|---|---|
| | 0 (none) | 1 minimal | 2 mild | 3 moderate | 4 severe |
| Endothelial Loss | Intact endothelium | <10% of the vessel circumference | 10-40% | 40-75% | >75% |
| Internal elastic lamina | Normal | Focal disruption of | Focal tear of IEL with | Tear of IEL with | Multiple areas of tearing of |

TABLE 1-continued

Semi-quantitative scoring of artery lesion parameters

| | Scored Parameter | | | | |
|---|---|---|---|---|---|
| | 0 (none) | 1 minimal | 2 mild | 3 moderate | 4 severe |
| | | IEL | fibrin deposition | hemorrhage and or inflammation and or early thrombus formation | IEL |
| Medial Changes severity of lesion | Normal | Focal piknosis (pressure necrosis) | Focal necrosis with hemorrhage or minimal leukocyte infiltration | Locally extensive necrosis with hemorrhage and moderate leukocyte infiltration | Mural tear with hemorrhage, inflammation |
| Medial Changes (% of vessel circumference) | Normal | <25% of the vessel circumference | 25-50% | 51-75% | >75% |
| Adventitia, necrosis/tearing | Normal | <25% of the vessel circumference | 25-50% | 51-75% | >75% |

Table 2 below summarizes the histological findings for samples T1-T4

TABLE 2

Semi-quantitative analysis of pathologic changes in the artery

| Sample | Cut | Endothelium | IEL | Media | Media circumference | Adventitia |
|---|---|---|---|---|---|---|
| T1 | 1 | 0 | 0 | 0 | 0 | 0 |
| | 2 | 0 | 0 | 0 | 0 | 0 |
| | 3 | 1 | 0 | 0 | 0 | 0 |
| | 4 | 1 | 0 | 0 | 0 | 0 |
| | 5 | 1 | 0 | 0 | 0 | 0 |
| | 6 | 1 | 0 | 0 | 0 | 0 |
| T2 | 1 | 4 | 0 | 0 | 0 | 0 |
| | 2 | 4 | 0 | 0 | 0 | 0 |
| | 3 | 4 | 1 | 1 | 1 | 0 |
| | 4 | 4 | 1 | 1 | 1 | 0 |
| | 5 | 3 | 0 | 0 | 0 | 0 |
| | 6 | 2 | 0 | 0 | 0 | 0 |
| T3 | 1 | 0 | 0 | 0 | 0 | 0 |
| | 2 | 0 | 0 | 0 | 0 | 0 |
| | 3 | 1 | 0 | 0 | 0 | 0 |
| | 4 | 0 | 0 | 0 | 0 | 0 |
| | 5 | 0 | 0 | 0 | 0 | 0 |
| | 6 | 0 | 0 | 0 | 0 | 0 |
| T4 | 1 | 1 | 0 | 0 | 0 | 0 |
| | 2 | 1 | 0 | 0 | 0 | 0 |
| | 3 | 2 | 0 | 1 | 1 | 0 |
| | 4 | 4 | 0 | 0 | 0 | 0 |
| | 5 | 4 | 0 | 0 | 0 | 0 |
| | 6 | 1 | 0 | 0 | 0 | 0 |

T1—There was minimal epithelial sloughing in cuts 3 to 6, involving less than 5% of the lumen circumference, with no evidence of thrombus formation. Overall, the artery was within normal ranges.

T2—sloughing of the endothelium was observed in all cuts. In cut 3 there was a single focus of apparent loss of continuity of the IEL with focal piknosis of underlying smooth muscle in the tunica media, and focal pale staining of the cytoplasm, suggesting acute necrosis. In cut 4 there was similar loss of continuity of the IEL with focal piknosis of smooth muscle. However, there was no evidence of leukocyte infiltration, and no fibrin deposition or early thrombus formation. The areas of loss of continuity of the IEL were confirmed on elastica stain. The arterial wall appeared to be within normal ranges in all remaining cuts.

T3—There was minimal epithelial sloughing in cuts 3 to 6, involving less than 5% of the lumen circumference, with no evidence of thrombus formation. Overall, the artery was within normal ranges.

T4—Cuts 1, 2, 3 and 6 were within normal ranges with minimal endothelial sloughing in foci. In cut 4 there was moderate endothelial sloughing with continuity of the IEL and a single focus of piknosis and pale staining of smooth muscle cells, suggesting acute pressure necrosis. There was however no evidence of leukocyte infiltration. Complete endothelial sloughing was observed in cuts 4 and 5.

CONCLUSIONS

Catheterization with the present device resulted in intact endothelium (FIG. 15A, arrows), a continuous IEL (FIG. 15B) and only two small foci of endothelium erosion covering less than 5% of the lumen circumference (FIG. 15C, arrows). On the otherhand, catheterization with the Nitinol device resulted in extensive endothelial erosion (FIG. 15D, arrows), loss of continuity of the IEL (FIG. 15E, arrow) and a single focus of endothelial necrosis (FIG. 15F, arrow).

Thus, catheterization using the present device minimally impacted the integrity of the vessel wall, while on the otherhand, catheterization using the Nitinol device resulted in widespread erosion of the intima, pressure necrosis and disruption of the IEL.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A device for use within an occluded biological vessel comprising an elongated body having a plurality of projections arranged around a distal portion of said elongated body, wherein each of said plurality of projections includes a leaf-like structure having a concave internal surface curved along a width of said leaf-like structure thereby enabling said leaf-like structure to trap a volume of occlusion material between said leaf-like structure and said elongated body and further wherein each of said projections is connected to said elongated body via a stem portion having an axial rigidity higher than said leaf-like structure.

2. The device of claim 1, wherein said projections are angled toward a proximal end of said elongated body.

3. The device of claim 1, wherein said projections are capable of folding against said device body when advanced distally through an occlusion in the biological vessel.

4. The device of claim 1, wherein said leaf-like structures are capable of scooping said thrombus material when said projections are embedded within said thrombus and said elongated body is pulled in a proximal direction.

5. The device of claim 1, wherein said leaf-like structure and said stem portion are co-molded from silicone.

6. The device of claim 5, wherein said stem portion is composed of a higher Shore silicone.

7. The device of claim 1, wherein said leaf-like structure of said projections includes an inward curving distal tip.

8. The device of claim 1, further comprising a lumen extending between a distal end and a proximal portion of the device, said lumen being for enabling blood flow around an occlusion in a blood vessel when the device is positioned in said blood vessel with said distal portion within said occlusion.

* * * * *